(12) United States Patent
Park

(10) Patent No.: US 9,078,952 B2
(45) Date of Patent: Jul. 14, 2015

(54) METHOD OF MANUFACTURING BONE GRAFT MATERIALS AND BONE GRAFT MATERIALS MANUFACTURED THEREBY

(76) Inventor: Ki-Deog Park, Suncheon-si (KR)

( * ) Notice: Subject to any disclaimer, the term of this patent is extended or adjusted under 35 U.S.C. 154(b) by 248 days.

(21) Appl. No.: 13/545,617

(22) Filed: Jul. 10, 2012

(65) Prior Publication Data

US 2013/0266616 A1 Oct. 10, 2013

(30) Foreign Application Priority Data

Apr. 9, 2012 (KR) ........................ 10-2012-0036966

(51) Int. Cl.
*A61L 27/12* (2006.01)
*A61L 27/32* (2006.01)
*A61L 27/58* (2006.01)
*C23C 14/06* (2006.01)
*A61L 27/30* (2006.01)

(52) U.S. Cl.
CPC ............... *A61L 27/12* (2013.01); *A61L 27/306* (2013.01); *A61L 27/32* (2013.01); *A61L 27/58* (2013.01); *C23C 14/06* (2013.01); *A61L 2430/02* (2013.01)

(58) Field of Classification Search
USPC ......................................................... 424/400
See application file for complete search history.

(56) References Cited

U.S. PATENT DOCUMENTS

| | | | |
|---|---|---|---|
| 7,452,566 B2 * | 11/2008 | Sul | 427/2.26 |
| 2007/0213832 A1 * | 9/2007 | Wen | 623/23.5 |
| 2008/0249638 A1 * | 10/2008 | Asgari | 623/23.75 |
| 2010/0312355 A1 * | 12/2010 | Yahav et al. | 623/23.61 |
| 2013/0078476 A1 * | 3/2013 | Riman et al. | 428/469 |

* cited by examiner

Primary Examiner — Gina Justice
(74) Attorney, Agent, or Firm — Quarles & Brady, LLP

(57) ABSTRACT

Bone graft materials include a bone-grafting material, which encourages regeneration of a missing bone tissue while being absorbed by the missing bone tissue, and a coating material, which is composed of at least one selected from the group consisting of magnesium, calcium hydroxyapatite, and mixtures thereof.

4 Claims, 3 Drawing Sheets

METHOD OF MANUFACTURING BONE GRAFT MATERIALS AND BONE GRAFT MATERIALS MANUFACTURED THEREBY

CROSS REFERENCE TO RELATED APPLICATION

The present application claims priority from Korean Patent Application Number 10-2012-0036966 filed on Apr. 9, 2012, the entire contents of which application are incorporated herein for all purposes by this reference.

BACKGROUND OF THE INVENTION

1. Field of the Invention

The present invention relates to a method of manufacturing bone graft materials and bone graft materials manufactured thereby, and more particularly, to a method of manufacturing bone graft materials, which are efficiently delivered, are strongly resistant to infection, and have excellent ability to encourage bone growth, and to bone graft materials manufactured thereby.

2. Description of Related Art

Bone grafting is used to fill cavities inside a bone tissue that is damaged due to bone diseases or bone ailments, including bone tumors, or to induce bone fracture healing, bone healing and joint fixation. Recently, in response to the increase in the population of elderly people and the improvement in the quality of life due to the development of industry and medical science, the necessity for bone grafting is gradually increasing.

In response to this trend, the development of a variety of graft materials, such as autogenous bone graft materials, allogenic bone graft materials, xenogenic bone graft materials, and alloplastic bone graft materials, is underway.

Although autogenous bone graft materials have merits in that almost no immune rejection response occurs and in that osteoconduction and osteoinduction are excellent because almost no bone is absorbed, owing to the fact that autogenous cancellous bone (ACB) is grafted, the drawbacks are that a surgical operation must be performed on a region other than the region in which bone is missing, and in that only a small amount of grafting material can be acquired from a graftee because the bone graft materials must be acquired from the graftee himself/herself.

Allogenic bone graft materials or xenogenic bone graft materials have merits in that they can overcome the drawbacks of autogenous bone graft materials because they involve allografting in which bone from other people is used rather than bone from the graftee, or xenografting in which bone from other animals is used rather than bone from the graftee. However, cells, blood, lipid layers, and the like, which cause an immune rejection response, must be removed from the grafting material, and demineralization, which may induce the activation of bone morphogenetic proteins (BMPs) that participate in osteoinduction, must be carried out. In addition to these burdens, there is a further drawback in that the danger of an unexpected genetic disease or protein disease cannot be excluded.

Therefore, these days, the development of alloplastic bone graft materials, which can be easily delivered and are more resistant to infection, is most active. Since alloplastic bone graft materials have the problem of insufficient ability to encourage bone growth compared to the above-described materials, such as autogenous bone graft materials, allogenic bone graft materials, and xenogenic bone graft materials, a number of studies are underway in order to overcome this problem.

The information disclosed in this Background of the Invention section is only for the enhancement of understanding of the background of the invention, and should not be taken as an acknowledgment or any form of suggestion that this information forms a prior art that would already be known to a person skilled in the art.

BRIEF SUMMARY OF THE INVENTION

Various aspects of the present invention provide a method of manufacturing bone graft materials, which are efficiently delivered, are strongly resistant to infection, and have excellent ability to encourage bone growth, and to bone graft materials manufactured thereby.

The technical objects that the invention aims to solve are not limited to the foregoing technical objects, and other technical objects, which have not been mentioned above, will be more fully apparent to a person having ordinary skill in the art from the following description.

In an aspect of the present invention, provided is a method of manufacturing bone graft materials that includes the following steps of: preparing a bone-grafting material; selecting at least one selected from the group consisting of magnesium, calcium hydroxyapatite, and mixtures thereof as a coating material; and applying the coating material as a thin film coating on the surface of the prepared bone-grafting material. The thickness of the coating material varies depending on the rate of absorption of the bone-grafting material in a region in which a missing bone tissue is located.

In an exemplary embodiment, the step of preparing the bone-grafting material may prepare an alloplastic bone-grafting material as the bone-grafting material, the alloplastic bone-grafting material being formed of beta-tricalcium phosphate granules having a size ranging from 250 µm to 1000 µm.

In an exemplary embodiment, the step of applying the coating material may include forming a thin film coating of the magnesium first and then forming a thin film coating of the calcium hydroxyapatite, the magnesium and the calcium hydroxyapatite being selected from the group consisting of magnesium, calcium hydroxyapatite, and mixtures thereof. The step of applying the coating material may apply the coating material such that the thickness of the coating material is thinner as the rate of absorption of the bone-grafting material in a region in which the missing bone tissue is located is faster.

Furthermore, the step of applying the coating material may apply the coating material as a thin film coating on the surface of the bone-grafting material via sputtering.

In another aspect of the present invention, provided are bone graft materials manufactured by the method of manufacturing bone graft materials as described above.

In a further aspect of the present invention, provided are bone graft materials that include a bone-grafting material, which encourages regeneration of a missing bone tissue while being absorbed by the missing bone tissue; and a coating material, which is composed of at least one selected from the group consisting of magnesium, calcium hydroxyapatite, and mixtures thereof.

In an exemplary embodiment, the bone-grafting material may be an alloplastic bone-grafting material composed of beta-tricalcium phosphate granules having a size ranging from 250 µm to 1000 µm, and the coating material includes a first thin film coating of magnesium and a second thin film coating of calcium hydroxyapatite.

In an exemplary embodiment, the thickness of the coating of the coating material may be thinner as the rate of absorption of the bone-grafting material in the missing bone tissue is faster.

According to embodiments of the invention, the method of manufacturing bone graft materials and the bone graft materials manufactured thereby have merits, such as efficient delivery and strong resistance to infection, since an alloplastic bone-grafting material, such as beta tricalcium phosphate, is used as a bone-grafting material.

In addition, according to embodiments of the invention, the method of manufacturing bone graft materials and the bone graft materials manufactured thereby have merits in that the ability to encourage bone growth is significantly improved by coating a bone-grafting material with a thin film of a coating material.

The methods and apparatuses of the present invention have other features and advantages which will be apparent from, or are set forth in greater detail in the accompanying drawings, which are incorporated herein, and in the following Detailed Description of the Invention, which together serve to explain certain principles of the present invention.

DETAILED DESCRIPTION OF THE INVENTION

Reference will now be made in detail to various embodiments of the present invention, examples of which are illustrated in the accompanying drawings and described below. In the following description of the present invention, detailed descriptions of known functions and components incorporated herein will be omitted when they may make the subject matter of the present invention unclear.

First, referring to FIG. 1 and FIG. 2, the structure of an embodiment of bone graft materials according to the invention will be described in detail. Here, FIG. 1 is a schematic view showing the process in which a missing bone tissue is regenerated using the bone graft materials of the invention, and FIG. 2 is a cross-sectional view schematically showing the structure of the bone graft materials of the invention.

Figure 1:
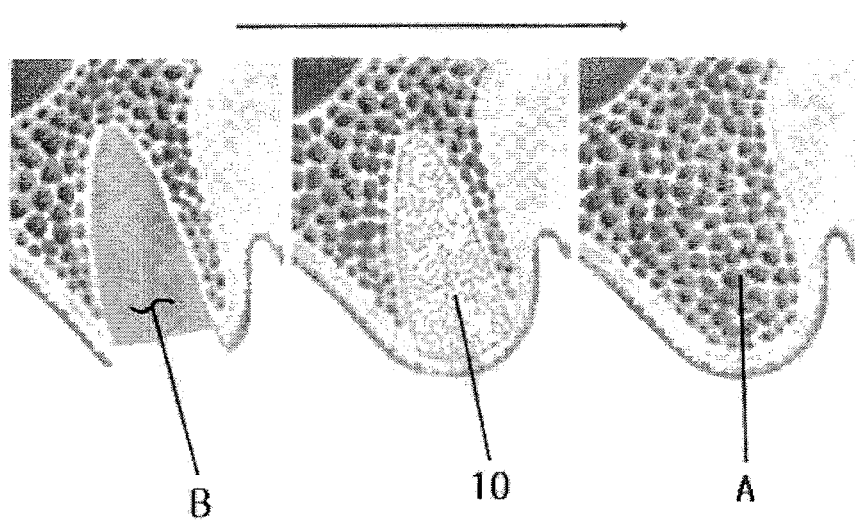
FIG. 1 is a schematic view showing the process in which a missing bone tissue is regenerated using an embodiment of bone graft materials according to the invention.
Figure 2:
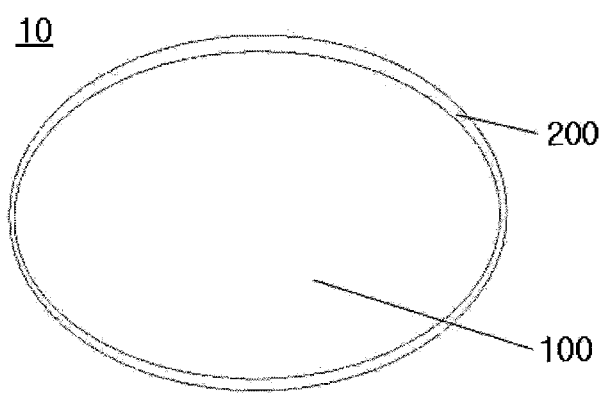
FIG. 2 is a cross-sectional view schematically showing the structure of an embodiment of the bone graft materials according to the invention.

As shown in FIG. 1 and FIG. 2, an embodiment of the bone graft materials according to the invention includes a bone-grafting material 100 and a coating material 200.

The bone-grafting material 100 is a component that is to be absorbed into the missing bone tissue B, such that the missing bone tissue B can be regenerated, and may be made of a variety of materials that can form alloplastic bone.

Among the variety of materials, beta-tricalcium phosphate ($\beta$-TCP: $\beta$-$Ca_3PO_4$) is most advantageous for forming the bone-grafting material 100, since alloplastic bone made of beta-tricalcium phosphate can be completely absorbed by the body.

However, when the alloplastic bone made of beta-tricalcium phosphate is used as the bone-grafting material 100, the ability to encourage bone growth may be degraded because the rate of absorption due to hydrolysis is faster than the rate of physiological absorption by osteoblasts (bone-forming cells). Therefore, the coating material 200 to be described later compensates for this.

More specifically, in order to restore the missing bone tissue B, among osteoblasts, the formation of cells that are important for initial bone formation (i.e. cells that begin cell activity after being fixed to a base; anchorage-dependent cells) is important. When only the bone-grafting material 100 made of beta-tricalcium phosphate is implanted in the missing bone tissue B, the ability to encourage bone growth is degraded because the rate of hydrolysis of beta-tricalcium phosphate is faster than the rate at which anchorage-dependent cells, which are important for initial bone formation, are formed. In contrast, when the bone-grafting material 100 is coated with the coating material 200 to be described later, the ability to encourage bone growth can be improved because the rate of hydrolysis of beta-tricalcium phosphate can be decelerated.

Here, the bone-grafting material 100 of the alloplastic bone made of beta-tricalcium phosphate may have the shape of granules having a size ranging from 250 μm to 1000 μm.

The reason why the bone-grafting material 100 having the shape of granules can be manufactured at a size that is significantly smaller than that of bone graft materials of the related art is that the rate of physiological absorption by osteoblasts and the rate of hydrolysis of beta-tricalcium phosphate can be controlled based on the thickness of the coating material 200. It is not necessary to manufacture the bone-grafting material in a relatively large size unlike bone graft materials of the related art, the size of which is determined in consideration of hydrolysis. This will be described later in detail in an embodiment of the method of manufacturing bone graft materials, which serves to manufacture the bone graft materials of the invention.

In the meantime, the coating material 200 is a component that is applied as a thin film coating on the surface of the bone-grafting material 100, thereby improving the ability of the bone-grafting material 100 to encourage bone growth at an early stage. The coating material 200 is made of at least one selected from among magnesium (Mg), calcium hydroxyapatite ($Ca_{10}[PO_4]_6[OH]_2$) and mixtures thereof.

As described above, the coating material 200 not only improves the ability of the bone-grafting material 100 to encourage bone growth by decelerating the rate of absorption thereof due to hydrolysis such that it is slower than the rate of physiological absorption by osteoblasts, but also performs the following additional functions.

Specifically, Mg serves not only to help an embodiment of the bone-grafting material of the invention adhere to the surface of the missing bone tissue B, but also to stimulate the proliferation of osteoblasts, in the same manner as insulin. Furthermore, Mg also serves to stabilize the structure of DNA and RNA as a cofactor of nucleic acids that are found in osteoblasts.

In addition, calcium hydroxyapatite also serves not only to help an embodiment of the bone-grafting material of the invention adhere to the surface of the missing bone tissue B, but also to enable an embodiment of the bone-grafting material of the invention to initially act so as to form cells that are important for initial bone formation.

However, although Mg and calcium hydroxyapatite, which constitute the coating material 200, have excellent abilities, such as the ability to facilitate adherence to the surface of the missing bone tissue B and the additional role of encouraging initial bone growth, they cannot be used as final bone graft materials because they act merely as cofactors or are not biodegraded.

In an example, unlike an embodiment of the bone graft materials of the invention in which calcium hydroxyapatite of the coating material 200 is applied as a thin film coating on the bone-grafting material 100, some of bone graft materials of the related art were manufactured by simply mixing beta-tricalcium phosphate, which forms the bone-grafting material 100, and calcium hydroxyapatite, which forms the coating material 200, at a predetermined ratio. However, calcium hydroxyapatite was not biodegraded but still present in a regenerated bone tissue A, which was problematic.

Therefore, Mg, calcium hydroxyapatite and the mixtures thereof as described above are advantageously used as the coating material 200 that is applied as a thin film coating on the bone-grafting material 100.

In an embodiment of the bone graft materials of the invention, the coating material 200 is formed as a thin film coating on the bone-grafting material 100 such that the rate of absorption of the bone-grafting material 100 due to hydrolysis is decelerated such that it is slower than the rate of physiological absorption by osteoblasts, thereby improving the ability to encourage bone growth. Furthermore, Mg and calcium hydroxyapatite, which are not used as ultimate bone graft materials by themselves even though they can play important roles in bone growth, can be used in the manufacture of bone graft materials.

Although the coating material 200 as described above may form a thin film coating on the bone-grafting material 100, its configuration may vary depending on the rate of absorption of the bone-grafting material 100 in the region in which the missing bone tissue B is located.

Specifically, when the rate of physiological absorption of the bone-grafting material 100 by osteoblasts is faster than the rate of hydrolysis of the bone-grafting material 100, it is not necessary for the coating material 200 to be formed thick in order to slow the absorption of the bone-grafting material 100 by osteoblasts. In contrast, when the rate of physiological absorption of the bone-grafting material 100 by osteoblasts is slower than the rate of hydrolysis of the bone-grafting material 100, it is not necessary for the coating material 200 to be formed thin, in which case the appropriate functions of the coating material 200 would not be sufficiently realized.

In other words, it is possible to manufacture an embodiment of the bone graft materials of the invention by adjusting the thickness of the coating material 200 depending on the rate of physiological absorption of the bone-grafting material 100 by osteoblasts and the rate of hydrolysis of the bone-grafting material 100.

Furthermore, in contrast, it is of course possible to realize an embodiment of the bone graft materials of the invention using the bone-grafting material 100 having the shape of granules that are significantly smaller than bone graft materials of the related art by adjusting the thickness of the coating material 200.

Aside from the feature in which the bone-grafting material 100 is coated with the coating material 200 by adjusting the thickness of the coating material 200, another feature in which the components of the coating material 200 are sequentially applied to form respective coatings may be considered.

Specifically, it is possible to form an Mg coating first, followed by a calcium hydroxyapatite coating. In this way, the role of calcium hydroxyapatite, which is advantageous in the formation of cells that are important for initial bone formation, is prominent when an embodiment of the bone graft materials of the invention initially acts on the missing bone tissue B. Afterwards, in the stage of bone growth, Mg plays a greater role, since it has the advantage of stabilizing the structure of DNA and RNA as a cofactor of nucleic acids that are found in osteoblasts.

Furthermore, since Mg is first applied, and then calcium hydroxyapatite is applied, calcium hydroxyapatite can prevent water-soluble Mg from being rapidly dissolved by the water that is present in the area of the missing bone tissue B and surrounding areas.

In other words, according to the technical features thereof, an embodiment of the bone graft materials of the invention not only enables Mg and calcium hydroxyapatite, which do not form the final bone graft materials by themselves, to be used as the coating material 200, but also enables Mg and calcium hydroxyapatite to be sequentially applied as coatings in consideration of the additional roles thereof.

Next, a detailed description will be given below of the method of manufacturing an embodiment of the bone graft materials of the invention as described above. Here, the individual steps enumerated to describe the manufacturing method are not necessarily conducted in the illustrated order. In some embodiments, it is of course possible to change the order of the individual steps or combine some of the steps.

Although not shown in the figures, an embodiment of the method of manufacturing bone graft materials of the invention includes a preparation step, a selection step and a coating step.

Here, the preparation step is the step of preparing the bone-grafting material 100, and it should be understood that the surrounding environment in which the bone-grafting material 100 is prepared is not specifically limited.

However, it should be noted that, when the prepared bone-grafting material 100 is the alloplastic bone-grafting material formed as beta-tricalcium phosphate granules having a size ranging from 250 μm to 1000 μm as described above, it may be subjected to hydrolysis when the surrounding area contains a large amount of moisture.

The selection step is the step of selecting at least one of Mg, calcium hydroxyapatite and mixtures thereof as the coating material 200. Like the foregoing preparation step, the surrounding environment is not specifically limited as long as it does not change the properties of the coating material 200.

However, when the following coating step is performed, first with Mg and then with calcium hydroxyapatite, it is advantageous to select and prepare these components such that it is easy to sequentially form coatings of these components.

In addition, the coating step is the step of coating the surface of the bone-grafting material 100 with the selected coating material 200, which is applied such that its thickness varies depending on the rate of absorption of the bone-grafting material in the region in which the missing bone tissue B is positioned.

In the coating step, it is advantageous to apply the coating material 200 thinner when the rate of absorption of the bone-grafting material in the region in which the missing bone tissue B is positioned is faster, such that bone graft materials manufactured in an embodiment of the method of manufacturing bone graft materials according to the invention can have a more excellent effect, as described above.

Furthermore, in the coating step, it is advantageous to apply Mg first and then to apply calcium hydroxyapatite so that Mg and calcium hydroxyapatite can play the individual additional roles described above.

However, although the coating step has a variety of technical characteristics as described above, if the coating material 200 is not applied as a thin film on the surface of the bone-grafting material 100, the function of the bone-grafting material 100 may be hindered by the coating material 200, which cannot be used as final bone graft materials because it acts merely as a cofactor or is not biodegraded.

Therefore, the coating step is assumed to be a thin film coating process. Although the thin film coating process may be performed in a variety of methods, when the bone-grafting material 100 is an alloplastic bone-grafting material composed of beta-tricalcium phosphate granules, a wet coating method using a solution is not preferable, because in such a case the bone-grafting material 100 would be decomposed by hydrolysis, and thus a thin film coating would not be properly formed.

Therefore, it is advantageous that the coating step be performed using a dry coating method. More specifically, a sputtering process is advantageous since it can form a thin film coating while excluding the possibility of hydrolysis of the bone-grafting material 100.

Here, the sputtering process refers to a method of ionizing and accelerating gas inside a vacuum vessel so that ions collide with a solid sample, thereby capturing atoms from the surface of the solid sample using the energy of the ions. The sputtering process is mainly used in attaching a metal thin film to the surface of an object such as glass.

Specifically, the coating step is carried out by powdering the coating material 200, which is at least one of Mg, calcium hydroxyapatite and mixtures thereof, to a predetermined size, and blowing the powdered coating material 200 with gas, such as nitrogen or argon, so that the powdered coating material 200 strikes at a high speed the surface of the bone-grafting material 100 in a vacuum chamber, which is decompressed to a pressure of $10^{-1}$ torr or lower, thereby forming a coating having a thickness of 30 μm or less on the surface of the bone-grafting material 100.

According to an embodiment of the method of manufacturing bone graft materials of the invention as described above, it is of course possible to manufacture embodiments of the bone graft materials of the invention that were described earlier.

Figure 3:
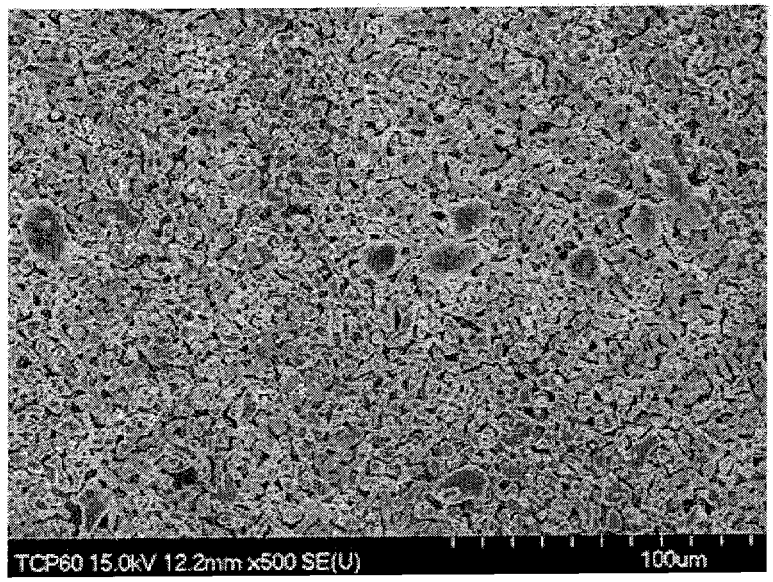
FIG. 3 is a picture taken at a magnification of 500 power, showing an example in which a missing bone tissue is regenerated using bone graft materials of the related art.
Figure 4:
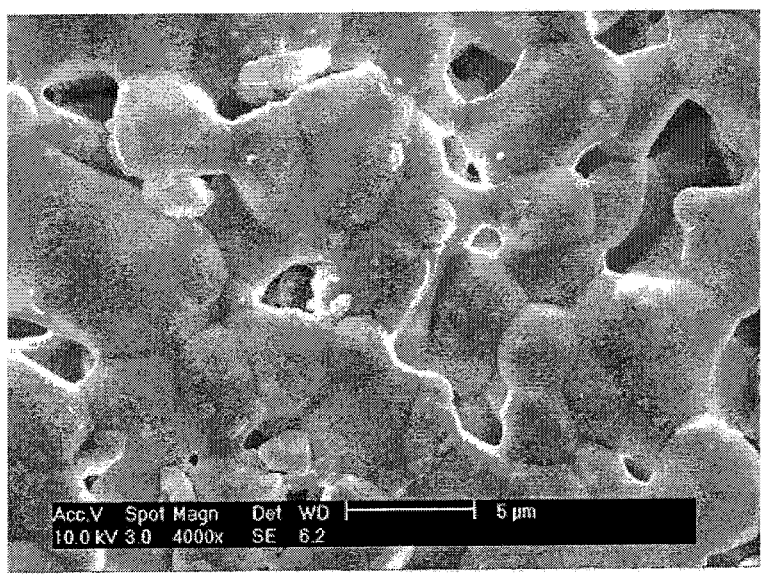
FIG. 4 is a picture taken at a magnification of 4000 power, showing an example in which a missing bone tissue is regenerated using bone graft materials of the related art.
Figure 5:
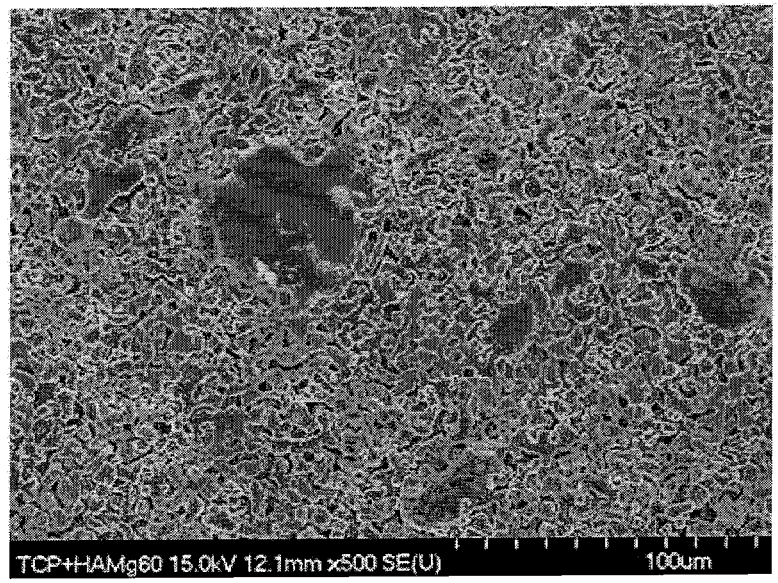
FIG. 5 is a picture taken at a magnification of 500 power, showing an example in which a missing bone tissue is regenerated using an embodiment of bone graft materials according to the invention.
Figure 6:
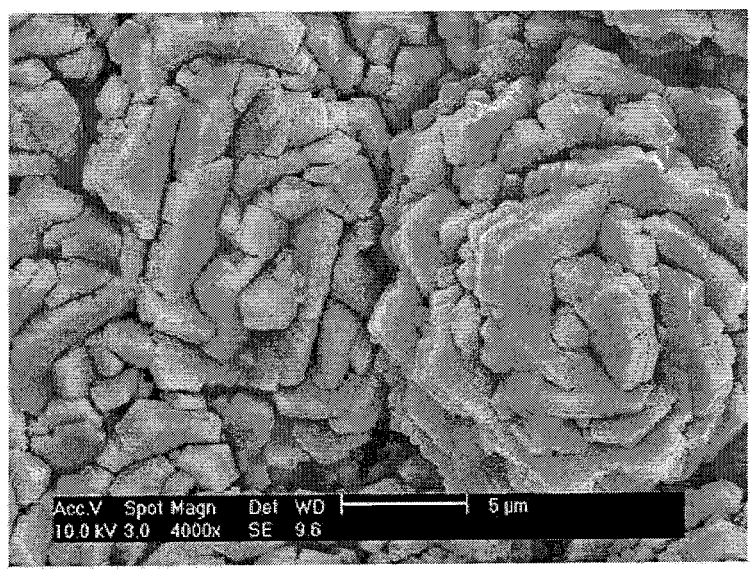
FIG. 6 is a picture taken at a magnification of 4000 power, showing an example in which a missing bone tissue is regenerated using an embodiment of bone graft materials according to the invention.

Finally, with reference to FIG. 3 to FIG. 6, the operation and effect of an embodiment of the bone graft materials according to the invention will be described in detail. Here, FIG. 3 and FIG. 4 are pictures taken at magnifications of 500 power and 4000 power, respectively, showing an example in which a missing bone tissue is regenerated using bone graft materials of the related art. FIG. 5 and FIG. 6 are pictures taken at magnifications of 500 power and 4000 power, respectively, showing an example in which a missing bone tissue is regenerated using an embodiment of bone graft materials according to the invention.

First, the operation of an embodiment of the bone graft materials of the invention will be described as follows.

As shown in FIG. 1, when the missing bone tissue B is filled with an embodiment of the bone graft materials of the invention, the coating material 200 adheres to the surface of the missing bone tissue B, and starts to form some cells of osteoblasts that are important for initial bone formation.

In this case, Mg of the coating material 200 stimulates the proliferation of osteoblasts, in the same manner as insulin, while stabilizing the structure of DNA and RNA as a cofactor of nucleic acids that are found in osteoblasts.

As the bone-grafting material 100 is gradually decomposed by hydrolysis, it starts to be absorbed by osteoblasts of the missing bone tissue B, helping the formation of cells that are important for initial bone formation. In this way, the bone-grafting material 100 helps the initially-formed bone grow and expand as time passes, so that the regenerated bone tissue A replaces the missing bone tissue B after a predetermined time passes.

Since the presence of the coating material 200 prevents the bone-grafting material 100 from being directly decomposed by hydrolysis, the bone-grafting material 100 can be sufficiently absorbed by osteoblasts, so that the effects thereof are significantly different from those of the bone graft materials of the related art, as will described below.

When the missing bone tissue B is regenerated using bone graft materials of the related art, a large amount of bone-grafting material is lost by hydrolysis before being absorbed by osteoblasts. Consequently, as shown in FIG. 3 and FIG. 4, the regenerated bone tissue forms therein a number of small clusters instead of one large lump, and has a subsidiary bone structure that is not crystallized.

However, when the missing bone tissue B is regenerated using an embodiment of the bone graft materials of the invention, the amount of the bone-grafting material 100 that is lost by hydrolysis can be minimized. Consequently, as shown in FIG. 5 and FIG. 6, the regenerated bone tissue forms therein one large lump instead of a number of small clusters, and has a subsidiary bone structure that is crystallized.

As set forth above, it is regarded that the difference between the effects of bone graft materials of the relate art and the effects of an embodiment of the bone graft materials of the invention is significant considering that bone regeneration spends a long time. This is because an embodiment of the bone graft materials of the invention is configured as described above.

While the present invention has been described and shown with respect to the specific embodiments, it will be apparent to a person having ordinary skill in the art that various modifications and variations may be made without departing from the spirit and scope of the invention. Therefore, such modifications and variations should not be construed as being separate from the technical spirit and scope of the invention, and it should be understood that such modified embodiments fall within the scope of the claims of the invention.

What is claimed is:

1. A method of manufacturing bone graft materials, comprising:
    preparing a bone-grafting material;
    forming a first thin film coating of magnesium having a thickness of 30 μm or less on the surface of the bone-grafting material; and
    forming a second thin film coating of calcium hydroxyapetite having a thickness of 30 μm or less on the surface of the first thin film.

2. The method of claim 1, wherein preparing the bone-grafting material comprises preparing an alloplastic bone-grafting material as the bone-grafting material, the alloplastic bone-grafting material being formed of beta-tricalcium phosphate granules having a size ranging from 250 μm to 1000 μm.

3. The method of claim 1, wherein the step of forming the first thin film, the second thin film, or both comprises applying the thin film coating on the surface of the bone-grafting material or on the first thin film via sputtering.

4. Bone graft materials manufactured by the method of manufacturing bone graft materials as recited in claim 1.

\* \* \* \* \*